(12) United States Patent
Phan et al.

(10) Patent No.: US 6,664,240 B2
(45) Date of Patent: Dec. 16, 2003

(54) TYLOSIN DERIVATIVES HAVING ANTIBACTERIAL ACTIVITY

(75) Inventors: Ly Tam Phan, Malden, MA (US); Marina V. Busuyek, Natick, MA (US); Yat Sun Or, Cambridge, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 10/002,918

(22) Filed: Nov. 15, 2001

(65) Prior Publication Data

US 2003/0096764 A1 May 22, 2003

(51) Int. Cl.[7] .......................... A61K 31/70; C07H 17/08
(52) U.S. Cl. ........................................... 514/30; 536/7.1
(58) Field of Search ............................... 536/7.1; 514/30

(56) References Cited

U.S. PATENT DOCUMENTS

| 4,820,694 A | 4/1989 | Debono et al. ............... 514/30 |
| 4,820,695 A | 4/1989 | Debono et al. ............... 514/30 |
| 5,545,624 A | 8/1996 | Hecker et al. ................ 514/30 |

FOREIGN PATENT DOCUMENTS

| EP | 0262903 A2 | 4/1988 |
| EP | 0262905 A2 | 4/1988 |

*Primary Examiner*—Elli Peselev
(74) *Attorney, Agent, or Firm*—Gastano D. Maccarone

(57) ABSTRACT

There are described novel substituted tylosin analogs and pharmaceutically acceptable compositions comprising a therapeutically effective amount of a compound of the invention in combination with a pharmaceutically acceptable carrier. Also described is a method for treating bacterial infections by administering to a mammal a pharmaceutical composition containing a therapeutically-effective amount of a compound of the invention, and processes for the preparation of such compounds.

8 Claims, No Drawings

TYLOSIN DERIVATIVES HAVING ANTIBACTERIAL ACTIVITY

TECHNICAL FIELD

The present invention relates to novel macrolides having antibacterial activity and useful in the treatment and prevention of bacterial infections. More particularly, the invention relates to a novel class of 4'-substituted 16-membered macrolides, compositions containing such compounds and methods for using the same, as well as processes for making such compounds.

BACKGROUND OF THE INVENTION

Macrolide antibiotics play a therapeutically important role, particularly with the emergence of new pathogens. Structural differences are related to the size of the lactone ring and to the number and nature (neutral or basic) of the sugars. Macrolides are classified according to the size of the lactone ring (12, 14, 15 or 16 atoms). The macrolide antibiotic family (14-, 15- and 16-membered ring derivatives) exhibits a wide range of characteristics (antibacterial spectrum, side-effects and bioavailability). Among the commonly used macrolides are erythromycin and josamycin.

The 16-membered ring macrolide antibiotics constitute an important clinically useful series of naturally occurring compounds within the macrolide class of antibiotics, as they show some advantages over 14-membered ring compounds (gastrointestinal tolerance and activity against strains expressing resistance of the inducible type). Sixteen membered macrolides usually contain an amino disaccharide—4-O-(L-mycarosyl)-D-mycaminose and/or D-desosamine. One class has only neutral sugars. The sixteen membered macrolides can be classified into two major groups—the leucomycins and the tylosin series. The tylosin series is divided into two groups- IIA and IIB which differ at the C-6-side chain and the nature of the sugars on the chromophore. Tylosin consists of a substituted 16-membered ring lactone (tylonolide), an aminosugar (D-mycaminose) attached to C-5, two neutral sugars (D-mycinose attached at C-23 and L-mycarose attached at C-4') and an acetaldehyde at C-6.

Considerable research efforts have been carried out on tylosin and its derivatives but not much success has been observed with this subclass. The search for macrolides active against MLS-resistant strains (MLS=Macrolides-Lincosamides-Streptogramines) has become a major goal, in addition to improving the overall profile of the macrolides in terms of acid stability, tolerance and pharmacokinetics.

SUMMARY OF THE INVENTION

The present invention provides a novel class of 4'-substituted and C20 modified tylosin analogs possessing increased antibacterial activity toward Gram positive and Gram negative bacteria as well as macrolide resistant Gram positives. In addition, the present invention provides a class of 4'-substituted tylosin derivatives that are more acid stable and overcome bacterial resistance.

In one embodiment, the present invention provides compounds of Formula I, or a pharmaceutically acceptable salt, ester or prodrug thereof, where Formula I is:

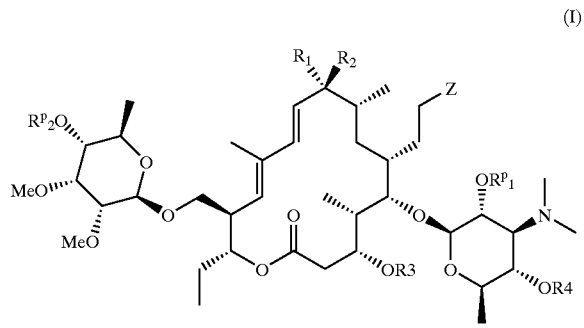

(I)

In Formula I:

Z is selected from the group consisting of:

(1) —NR7R8, wherein R7 and R8 are each independently selected from hydrogen, C1–C6-alkyl, optionally substituted with one or more substituents selected from the group consisting of halogen, aryl, substituted aryl, heterocyclic and substituted heterocyclic, C2–C6-alkenyl, optionally substituted with one or more substituents selected from the group consisting of halogen, aryl, substituted aryl, heterocyclic and substituted

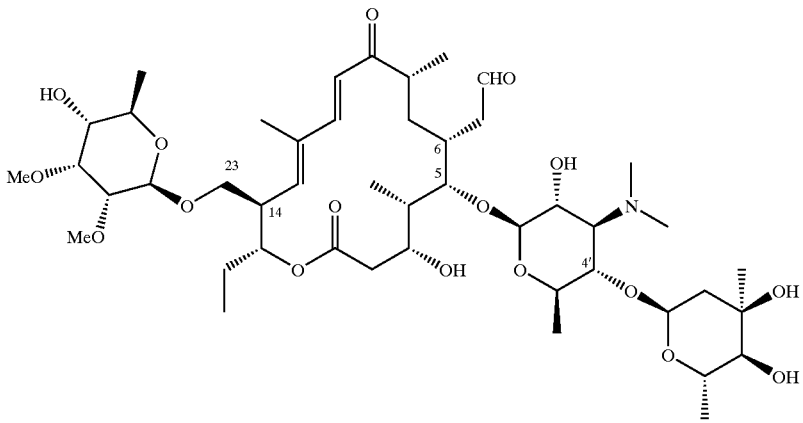

Tylosin heterocyclic, C2–C6-alkynyl, optionally substituted with one or more substituents selected from the group consisting of halogen, aryl, substituted aryl, heterocyclic and substituted heterocyclic or R7R8 taken with the nitrogen atom to which they are connected form a 3- to 7-membered ring which may optionally contain a hetero function selected from the group consisting of —O—, —NH—, —N(C1–C6-alkyl)-, —N(aryl)-, —N(heteroaryl)-, —S—, —S(O)— and —S(O)$_2$—;

(2) —NR7C(O)—R9, where R7 is as previously defined and R9 is selected from the group consisting of:
  (a) C1–C6-alkyl, optionally substituted with one or more substituents selected from the group consisting of halogen, aryl, substituted aryl, heterocyclic and substituted heterocyclic;
  (b) C2–C6-alkenyl, optionally substituted with one or more substituents selected from the group consisting of halogen, aryl, substituted aryl, heterocyclic and substituted heterocyclic;
  (c) C2–C6-alkynyl, optionally substituted with one or more substituents selected from the group consisting of halogen, aryl, substituted aryl, heterocyclic and substituted heterocyclic;
  (d) aryl;
  (e) substituted aryl;
  (f) heterocyclic; and
  (g) substituted heterocyclic;

(3) —NR7C(O)—NR8R9, where R7, R8, and R9 are as previously defined;

(4) —S(O)$_n$—R10, where R10 is selected from the group consisting of aryl, substituted aryl, heterocyclic and substituted heterocyclic and where n=0, 1 or 2;

(5) —S(O)$_n$—(C1–C6-alkyl), optionally substituted with one or more substituents selected from the group consisting of halogen, aryl, substituted aryl, heterocyclic and substituted heterocyclic, where n is as previously defined;

(6) —S(O)$_n$—(C2–C6-alkenyl), optionally substituted with one or more substituents selected from the group consisting of halogen, aryl, substituted aryl, heterocyclic and substituted heterocyclic, where n is as previously defined;

(7) —S(O)$_n$—(C2–C6-alkynyl), optionally substituted with one or more substituents selected from the group consisting of halogen, aryl, substituted aryl, heterocyclic and substituted heterocyclic, where n is as previously defined; and (8) —O—M—Y, where M is:
  (a) absent,
  (b) —C(O)—
  (c) —C(O)N(R7)-, where R7 is as previously defined,
  (d) —C1–C6-alkyl-N(R7)-, where R7 is as previously defined,
  (e) —C2–C6-alkenyl-N(R7)-, where R7 is as previously defined, or
  (f) —C2–C6-alkynyl-N(R7)-, where R7 is as previously defined
and where Y is:
  (a) hydrogen,
  (b) hydroxy protecting group,
  (c) C1–C6-alkyl, optionally substituted with one or more substituents selected from the group consisting of halogen, aryl, substituted aryl, heterocyclic and substituted heterocyclic,
  (d) C2–C6-alkenyl, optionally substituted with one or more substituents selected from the group consisting of halogen, aryl, substituted aryl, heterocyclic and substituted hetreocyclic,
  (e) C2–C6-alkynyl, optionally substituted with one or more substituents selected from the group consisting of halogen, aryl, substituted aryl, heterocyclic and substituted heterocyclic,
  (f) aryl,
  (g) substituted aryl,
  (h) heterocyclic, or
  (i) substituted heterocyclic;

R1 and R2 are each independently selected from the group consisting of:
  (a) hydrogen;
  (b) hydroxy;
  (c) protected hydroxy;
  (d) OC(O)—C1–C12-alkyl, optionally substituted with one or more substituents selected from the group consisting of halogen, aryl, substituted aryl, heterocyclic, substituted heterocyclic, O—R7 and NR7R8 where R7 and R8 are as previously defined;
  (e) O—R7, where R7 is as previously defined;
  (f) halogen;
  (g) R1 and R2 taken together are oxo; and
  (h) NR7R8, where R7 and R8 are as previously defined;

R3 is selected from the group consisting of:
  (l) hydrogen;
  (2) a hydroxy protecting group;
  (3) —C(O)—C1–C12-alkyl, optionally substituted with one or more substituents selected from the group consisting of halogen, aryl, substituted aryl, heterocyclic, substituted heterocyclic, O-R7 and NR7R8 where R7 and R8 are as previously defined;
  (4) C1–C6-alkyl, optionally substituted with one or more substituents selected from the group consisting of halogen, aryl, substituted aryl, heterocyclic, substituted heterocyclic, O—R7 and NR7R8 where R7 and R8 are as previously defined;
  (5) C2–C6-alkenyl, optionally substituted with one or more substituents selected from the group consisting of halogen, aryl, substituted aryl, heterocyclic, substituted heterocyclic, O—R7 and NR7R8 where R7 and R8 are as previously defined; and
  (6) C2–C6-alkynyl, optionally substituted with one or more substitutents selected fron the group consisting of halogen, aryl, substituted aryl, heterocyclic, substituted heterocyclic, O—R7 and NR7R8 where R7 and R8 are as previously defined;

R4 is —M—Y, where M and Y are as previously defined; and $R^P_1$ and $R^P_2$ are each independently hydrogen or a hydroxy protecting group.

In another embodiment, the present invention provides a process for preparing novel compounds represented by Formula I wherein the groups Z, R1, R2, R3, R4, $R^P_1$ and $R^P_2$, are as previously defined.

DETAILED DESCRIPTION OF THE INVENTION

A first embodiment of the invention is a compound represented by Formula I as described above.

Representative compounds of the invention are those selected from the group consisting of:

Compound of Formula I: Z=—OCH$_2$CH=CH$_2$, R1 and R2 taken together=O, R3=H, $R^P_1$=H, $R^P_2$=H and R4=H;

Compound of Formula I: Z=—OCH$_2$CH=CH-phenyl, R1 and R2 taken together=O, R3=H, $R^P_1$=H, $R^P_2$=H and R4=H;

Compound of Formula I: Z=—OCH$_2$CH=CH-phenyl, R1 and R2 taken together=O, R3=—CH$_3$, R4=H, R$^P_1$=H and R$^P_2$=H;

Compound of Formula I: Z=—OCH$_2$CH=CH-phenyl, R1 and R2 taken together=O, R3=H, R4=—CH$_2$C≡CH, R$^P_1$=H and R$^P_2$=H;

Compound of Formula I: Z=—OCH$_2$CH=CH-phenyl, R1 and R2 taken together=O, R3=H, R4=—CH$_2$C≡C-(2-pyridyl), R$^P_1$=H and R$^P_2$=H;

Compound of Formula I: Z=—OCH$_2$CH=CH-phenyl, R1 and R2 taken together=O, R3=H, R4=—CH$_2$C≡C-(3-quinolyl), R$^P_1$=H and R$^P_2$=H;

Compound of Formula I: Z=—OCH$_2$CH=CH-phenyl, R1 and R2 taken together=O, R3=—CH$_3$, R4=—CH$_2$CH=CH$_2$, R$^P_1$=H and R$^P_2$=H;

Compound of Formula I: Z=—OCH$_2$CH=CH-phenyl, R1 and R2 taken together=O, R3=—CH$_3$, R4=—CH$_2$CH=CH-(3-pyridyl), R$^P_1$=H and R$^P_2$=H;

Compound of Formula I: Z=—OC(O)CH$_2$-(4-chlorophenyl), R1 and R2 taken together=O, R3=H, R$^P_1$=H, R$^P_2$=H and R$^P$4=H;

Compound of Formula I: Z=—OC(O)CH$_2$-(4-chlorophenyl), R1 and R2 taken together=O, R3=H, R4=—CH$_2$CH=CH$_2$, R$^P_1$=H and R$^P_2$=H;

Compound of Formula I: Z=—OC(O)CH$_2$-(4-chlorophenyl), R1 and R2 taken together=O, R3=H, R4=—CH$_2$CH=CH-(3-pyridyl), R$^P_1$=H and R$^P_2$=H;

Compound of Formula I: Z=—NHCH$_2$C≡CH, R1 and R2 taken together=O, R3=H, R$^P_1$=H, R$^P_2$=H and R4=H;

Compound of Formula I: Z=—NHCH$_2$C≡C-(3-quinolyl), R1 and R2 taken together=O, R3=H, R$^P_1$=H, R$^P_2$=H and R4=H;

Compound of Formula I: Z=—N(CH$_3$)CH$_2$C≡C-(3-quinolyl), R1 and R2 taken together=O, R3=H, R$^P_1$=H, R$^P_2$=H and R4=H; and Compound of Formula I: Z=—N(CH$_3$)CH$_2$C≡C-(3-quinolyl), R1 and R2 taken together=O, R3=—CH$_3$, R4=H, R$^P_1$=H and R$^P_2$=H.

Definitions

The terms "C$_1$–C$_3$-alkyl," "C$_1$–C$_6$-alkyl" or "C1–C12-alkyl," as used herein, refer to saturated, straight- or branched-chain hydrocarbon radicals containing between one and three, one and six or one and twelve carbon atoms, respectively. Examples of C$_1$–C$_3$ alkyl radicals include, but are not limited to, methyl, ethyl, propyl and isopropyl, and examples of C$_1$–C$_6$-alkyl radicals include, but are not limited to, methyl, ethyl, propyl, isopropyl, n-butyl, tert-butyl, neopentyl and n-hexyl, and examples of C1–C12-alkyl radicals include, but are not limited to, methyl, ethyl, propyl, isopropyl, n-butyl, tert-butyl, neopentyl, n-hexyl, n-octyl, n-decyl, and n-dodecyl.

The term "C2–C6-alkenyl," as used herein, refers to straight- or branched-chain hydrocarbon radicals containing between two and six carbon atoms with one or more double bonds in the chain. Examples of C2–C6-alkenyl include, but are not limited to, propenyl, isobutenyl, 1,3-hexadienyl, n-hexenyl, and 3-pentenyl.

The term "C2–C6-alkynyl," as used herein, refers to straight- or branched-chain hydrocarbon radicals containing between two and six carbon atoms with one or more triple bonds in the chain optionally containing one or more double bond. Examples of C2–C6-alkynyl include, but are not limited to, propynyl, isopentynyl, 1,3-hexadiynyl, n-hexynyl, 3-pentynyl, and 1-hexen-3-ynyl.

The term "C$_1$–C$_6$-alkoxy," as used herein, refers to a C$_1$–C$_6$-alkyl group, as previously defined, attached to the parent molecular moiety through an oxygen atom. Examples of C$_1$–C$_6$-alkoxy include, but are not limited to, methoxy, ethoxy, propoxy, isopropoxy, n-butoxy, tert-butoxy, neopentoxy and n-hexoxy.

The term "C$_1$–C$_3$-alkyl-amino," as used herein, refers to one or two C$_1$–C$_3$-alkyl groups, as previously defined, attached to the parent molecular moiety through a nitrogen atom. Examples of C$_1$–C$_3$-alkyl-amino include, but are not limited to, methylamino, dimethylamino, ethylamino, diethylamino, and propylamino.

The term "aprotic solvent," as used herein, refers to a solvent that is relatively inert to proton activity, i.e., not acting as a proton-donor. Examples include, but are not limited to, hydrocarbons, such as for example, hexane and toluene, and the like, halogenated hydrocarbons, such as, for example, methylene chloride, ethylene chloride, chloroform, and the like, heterocyclic compounds, such as, for example, tetrahydrofuran, N-methyl pyrrolidinone, and the like and ethers such as for example, diethyl ether, bis-methoxymethyl ether and the like. Such compounds are well known to those skilled in the art, and it will be apparent to those skilled in the art that individual solvents or mixtures thereof may be preferred for specific compounds and reaction conditions, for example, depending upon such factors as the solubility of reagents, reactivity of reagents and preferred temperature ranges. Further discussions of aprotic solvents may be found in organic chemistry textbooks or in specialized monographs, for example: *Organic Solvents Physical Properties and Methods of Purification*, 4th ed., edited by John A. Riddick et al., Vol. II, in the Techniques of Chemistry Series, John Wiley & Sons, NY, 1986.

The term "aryl," as used herein, refers to unsubstituted carbocyclic aromatic groups including, but not limited to, phenyl, 1- or 2-naphthyl and the like.

The terms "C$_3$–C$_5$–Cycloalkyl- and C$_3$–C$_7$–Cycloalkyl," as used herein refer to carbocyclic groups of 3 to 5 or 3 to 7 carbon atoms, respectively, such as for example, cyclopropyl, cyclobutyl, cyclopentyl, cyclohexyl, and cycloheptyl.

The term "C$_1$–C$_3$-alkyl-C$_3$–C$_5$–Cycloalkyl," as used herein refers to a C$_3$–C$_5$-cycloalkyl radical, as defined above, attached to a C$_1$–C$_3$-alkyl radical by replacement of a hydrogen atom on the latter.

The terms "halo" and "halogen," as used herein, refer to an atom selected from fluorine, chlorine, bromine and iodine.

The term "heteroaryl," as used herein, refers to a cyclic aromatic radical having from five to ten ring atoms of which one ring atom is selected from S, O and N; zero, one or more ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heterocycloalkyl," as used herein, refers to a non-aromatic 3-, 4-, 5-, 6- or 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "heterocyclic," as used herein, refers to heterocycloalkyl and heteroaryl. The term "substituted heterocyclic," as used herein, refers to substituted heterocycloalkyl and substituted heteroaryl.

The term "substituted aryl," as used herein refers to an aryl group, as defined herein, substituted by independent replacement of one or more of the hydrogen atoms therein with, for example, but not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_7$-cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, substituted aryl, heteroaryl, substituted heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$-$C_3$-alkyl-amino, thio, aryl-thio, heteroarylthio, benzyl-thio, $C_1$–$C_6$-alkyl-thio, or methylthiomethyl.

The term "substituted heteroaryl," as used herein refers to a heteroaryl group as defined herein substituted by independent replacement of one or more of the hydrogen atoms therein with, for example, but not limited to, F, Cl, Br, I, OH, $NO_2$, CN, C(O)—$C_1$-$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$-$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-Cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$-$C_3$-alkyl-amino, thio, aryl-thio, heteroarylthio, benzyl-thio, $C_1$–$C_6$-alkyl-thio, or methylthiomethyl.

The term "substituted heterocycloalkyl," as used herein, refers to a heterocycloalkyl group, as defined above, substituted by independent replacement of one or more of the hydrogen atoms therein with, for example, but not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$-$C_6$-alkyl, $C_3$–$C_6$-Cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$-$C_3$-alkyl-amino, thio, aryl-thio, heteroarylthio, benzyl-thio, $C_1$–$C_6$-alkyl-thio, or methylthiomethyl.

The term "substituted cycloalkyl," as used herein, refers to a $C_3$–$C_7$ cycloalkyl group, as defined above, substituted by independent replacement of one or more of the hydrogen atoms therein with, for example, but not limited to, F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$-$C_6$-alkyl, $C_3$–$C_6$-Cycloalkyl, $CF_3$, $CH_2CF_3$, $CH_2Cl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$-$C_3$-alkyl-amino, thio, aryl-thio, heteroarylthio, benzyl-thio, $C_1$–$C_6$-alkyl-thio, or methylthiomethyl.

"Hydroxy-protecting group," as used herein, refers to an easily removable group which is known in the art to protect a hydroxyl group against undesirable reaction during synthetic procedures and to be selectively removable. The use of hydroxy-protecting groups is well known in the art for protecting groups against undesirable reactions during a synthetic procedure and many such protecting groups are known. See, for example, T. H. Greene and P. G. M. Wuts, *Protective Groups in Organic Synthesis,* 3rd edition, John Wiley & Sons, New York (1999). Examples of hydroxy-protecting groups include, but are not limited to, methylthiomethyl, tert-dimethylsilyl, tert-butyldiphenylsilyl, acyl substituted with an aromatic group and the like.

The term "protected-hydroxy," refers to a hydroxy group protected with a hydroxy protecting group, as defined above, including, for example, but not limited to, benzoyl, acetyl, trimethylsilyl, triethylsilyl, methoxymethyl groups.

"Aldehyde-protecting group," as used herein, refers to an easily removable group which is known to protect an aldehyde group against undesirable reaction during synthetic procedures and to be selectively removable. The use of aldehyde-protecting groups is well known in the art for protecting aldehyde groups against undesirable reactions during a synthetic procedure and many such protecting groups are known. See, for example, T. H. Greene and P. G, M, Wuts, *Protective Groups in Organic Synthesis,* op. cit. Examples of aldehyde-protecting groups include, but are not limited to, acetals, ketals, O-substituted cyanohydrins, substituted hydrazones, imines and the like.

The term "protected aldehyde" refers to an aldehyde group protected with an aldehyde protecting group, as defined above, including, for example, but not limited to, dimethyl acetyl, 1,3-dioxolane, 1,3-dioxane and the like.

The term "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be apparent to those skilled in the art that individual solvents or mixtures thereof may be preferred for specific compounds and reaction conditions, for example, depending upon such factors as the solubility of reagents, reactivity of reagents and preferred temperature ranges. Further discussions of protogenic solvents may be found in organic chemistry textbooks or in specialized monographs, for example: *Organic Solvents Physical Properties and Methods of Purification,* 4th ed., edited by John A. Riddick et al., op. cit.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present. Further, in those cases where a bond between carbon atoms of the macrolide is a double bond both the cis and trans forms are within the scope of the invention described in this application.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences,* 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include formates, acetates, propionates, butyrates, acrylates and ethylsuccinates.

The term "pharmaceutically acceptable prodrugs," as used herein, refers to those prodrugs of the compounds of the present invention which are, within the scope of sound medical judgment, suitable for use in contact with the tissues of humans and lower animals without undue toxicity, irritation, allergic response and the like, commensurate with a reasonable risk/reward ratio, and effective for their intended use, as well as the zwitterionic forms, where possible, of the compounds of the invention. The term "prodrug" refers to compounds that are rapidly transformed in vivo to yield the parent compound of the above formulae, for example, by hydrolysis in blood. A thorough discussion is provided in T. Higuchi and V. Stella, *Prodrugs as Novel delivery Systems,* Vol. 14 of the A.C.S. Symposium Series and in Edward B. Roche, ed., *Bioreversible Carriers in Drug Design,* American Pharmaceutical Association and Pergamon Press, 1987, both of which are incorporated by reference herein.

Antibacterial Activity

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiter plates utilizing the appropriate Mueller Hinton Broth medium (CAMHB) for the observed bacterial isolates. Antimicrobial agents were serially diluted (2-fold) in DMSO to produce a concentration range from about 64 $\mu$g/ml to about 0.03 $\mu$g/ml. The diluted compounds (2 $\mu$l/well) were then transferred into sterile, uninoculated CAMHB (0.2 mL) by use of a 96 fixed tip-pipetting station. The inoculum for each bacterial strain was standardized to $5 \times 10^5$ CFU/mL by optical comparison to a 0.5 McFarland turbidity standard. The plates were inoculated with 10 $\mu$l/well of adjusted bacterial inoculum. The 96 well plates were covered and incubated at 35+/−2° C. for 24 hours in ambient air environment. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the range from about 64 $\mu$g/ml to about 0.03 $\mu$g/ml.

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, powders, capsules, pills, and granules can be prepared with coatings and shells such as enteric coatings and other coatings well known in the pharmaceutical formulating art. They may optionally contain opacifying agents and can also be of a composition whereby they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from about 0.01 to about 50 mg/kg body weight or more preferably from about 0.1 to about 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of the compounds of the present invention per day in single or multiple doses.

Abbreviations

Abbreviations which have been used in the descriptions of the scheme and the examples that follow are: AIBN for azobisisobutyronitrile; Bu$_3$SnH for tributyltin hydride; CDI for carbonyldiimidazole; DBU for 1,8-diazabicyclo[5.4.0]undec-7-ene; DEAD for diethylazodicarboxylate; DMF for dimethyl formamide; DMSO for dimethyl sulfoxide, DPPA for diphenylphosphoryl azide; EtOAc for ethyl acetate; MeOH for methanol; NaN(TMS)$_2$ for sodium bis(trimethylsilyl)amide; NMO for N-methylmorpholine N-oxide; TEA for triethylamine; THF for tetrahydrofuran; TPP for triphenylphosphine; DMAP for 4-N,N-dimethylamino pyridine; TFA for trifluoroacetic acid; KHMDS for potassium bis(trimethylsilyl)amide; Ac for acetyl; Bz for benzoyl; TBAF for tetrabutyl ammonium fluoride; m-CPBA for meta-chloro perbenzoic acid; TBDMS for tert-butyl dimethyl silyl; TES for triethylsilyl and TBDPS for tert-butyldiphenyl silyl.

Synthetic Methods

The compounds and processes of the present invention will be better understood in connection with the following synthetic schemes which are illustrative of the methods by which the compounds of the invention may be prepared. The groups Z, R1, R2, R3, R4, R7, R8, $R^P_1$ and $R^P_2$ are as defined previously, unless otherwise noted below.

Scheme 1

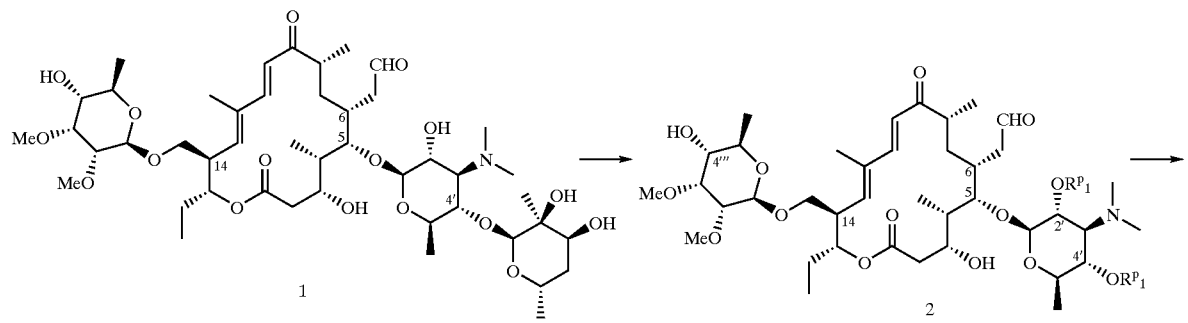

-continued

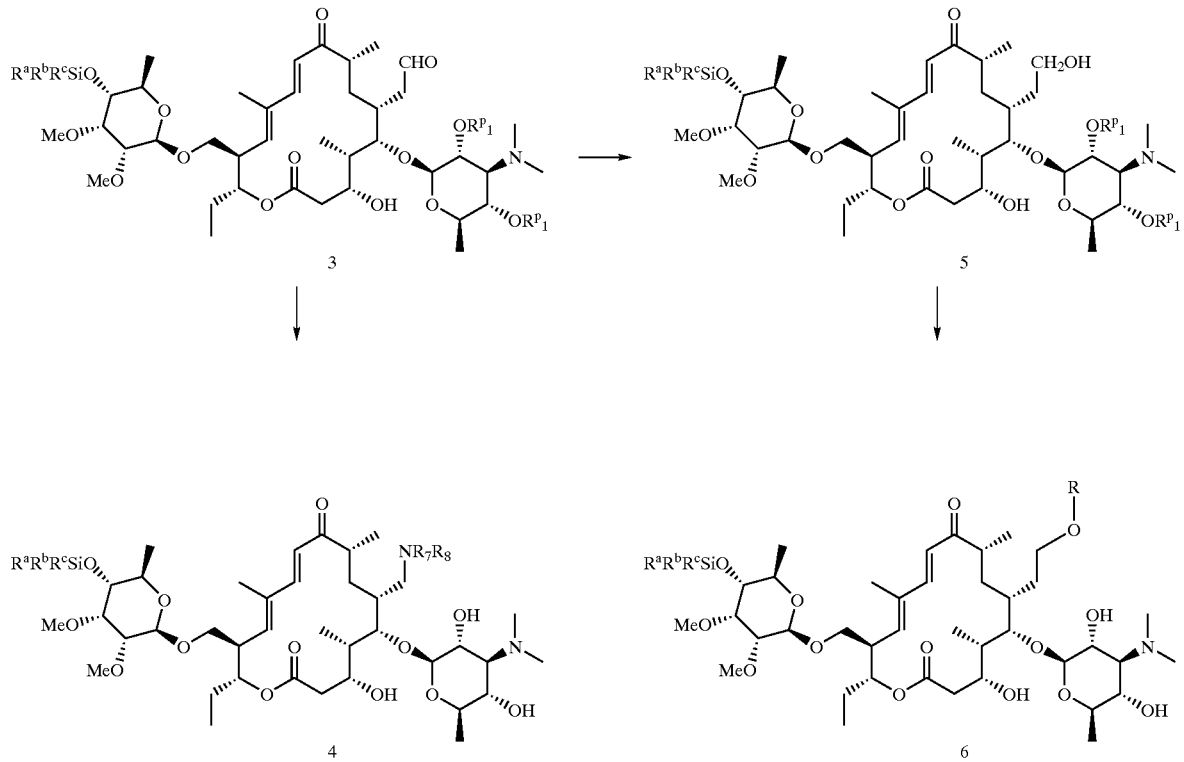

One process of the invention for the preparation of the compounds of Formula I comprises treating tylosin (compound 1 of Scheme 1) with dilute aqueous acids (0.1–5N) such as hydrochloric acid, sulfuric acid, trifluoroacetic acid, acetic acid or the like, optionally in an organic solvent such as acetone, acetonitrile, methanol, ethanol or the like, or combinations thereof, at from 0° C. to 100° C. for 1–24 hours to provide the unprotected compound 2 where $R^P_1$ is hydrogen. Compound 2 is protected as an ester where $R^P_1$ is an acetyl or benzoyl by reacting the unprotected compound 2 with acylating agents such as acetic anhydride, benzoic anhydride, acyl chloride, mixed anhydride and the like in an aprotic organic solvent such as methylene chloride, ethylene chloride, THF, chloroform, DMF, acetonitrile or the like at from 0° C. to 50° C. for 1–48 hours to provide compound 2, where $R^P_1$ is an ester. Compound 2 is further protected at 4' by treating with a silylating agent such as triethylsilyl chloride, TBDMSCl, TBDPSCl or the like, optionally with the addition of DMAP, imidazole or the like, in an aprotic solvent such as methylene chloride, ethylene chloride, THF, chloroform, DMF, acetonitrile or the like at from 0° C. to 50° C. for 1–48 hours to provide compound 3. Compound 3 can be further derivatized to an amino derivative via reductive amination methods by treating with an amine compound in the presence of sodium borohydride, sodium cyanoborohydride or the like in an alcoholic solvent such as methanol, ethanol or isopropanol or in acetonitrile or the like at a pH between from about 2 to about 6 to provide compound 4. Compound 3 can also be further reduced to a corresponding alcohol with various hydride reducing agents such as sodium borohydrides, lithium borohydrides or the like in an organic solvent such as methanol, ethanol, isopropanol, acetonitrile, THF or the like to provide compound 5. Compound 5 can be converted to an ether compound of the invention by treatment with an alkyl halide, alkyl sulphonate, propargyl halide, allyl halide, arylallyl halide, heteroarylallyl halide, benzyl halide or the like in the presence of a base such as sodium hydride, potassium hydride, potassium tert-butoxide, potassium hydroxide, KHMDS, or the like in an aprotic solvent such as THF, DMSO, DMF, dioxane, or the like or mixtures thereof, from about −20° C. to about 60° C. to provide compound 6. Compounds 4 and 6 can be deprotected with TBAF or hydrofluoric acid to remove the silyl protecting group followed by methanolysis at from room temperature to reflux to remove the $R^P_1$ protecting group at the 2'- and 4'-positions where $OR^P_1$ is ester or silyl ether to provide a compound of Formula I.

Scheme 1a

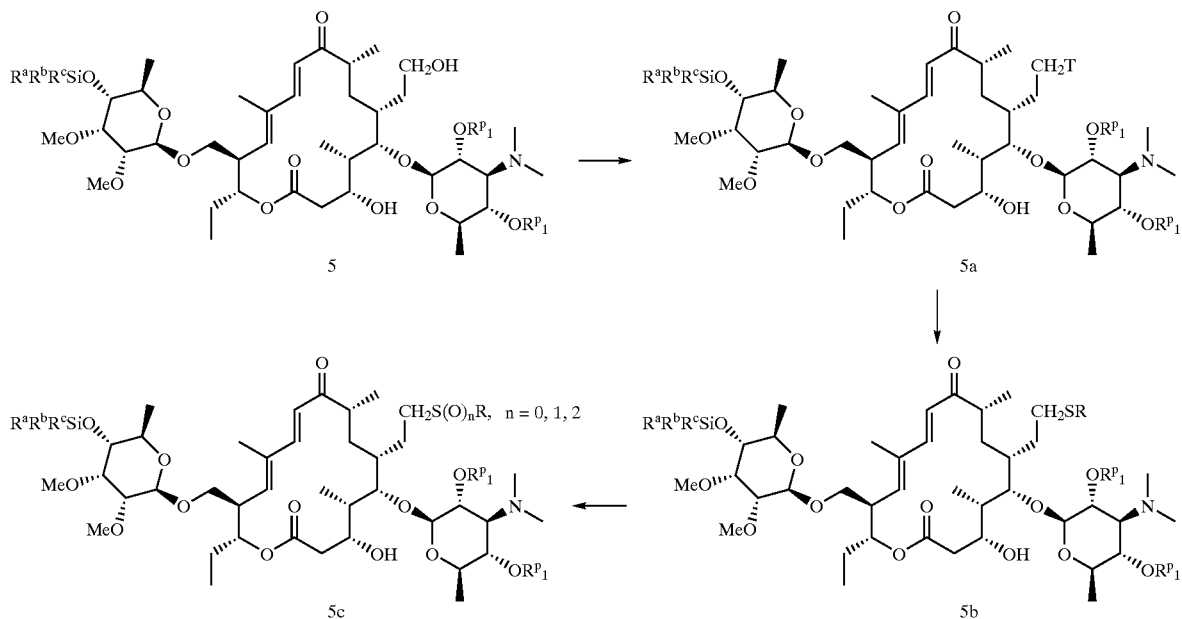

Another process of the invention, for the preparation of compounds of Formula I comprises treating compound 5 of Scheme 1 in an aprotic organic solvent such as methylene chloride, ethylene chloride, THF, chloroform, DMF, acetonitrile or the like with halogenating agents such as $PBr_3$, $CCl_4/PPh_3$, $CBr_4/PPh_3$ and the like at a temperature from about –20° C. to about 60° C. to provide compound 5a, where T is a halogen. Compound 5 can also be converted to the corresponding ester by standard techniques, for example, reacting compound 5 with an acid halide or an acid anhydride with a base, such as an amine base, at a temperature from about –20° C. to about 60° C. in an aprotic organic solvent. Compound 5a can be be reacted with a thiol containing compound in the presence of a base, such as sodium hydride, sodium hydroxide, potassium tert-butoxide and the like, in an organic solvent such as acetone, acetonitrile, methanol, ethanol or the like, or combinations thereof, at a temperature from about –20° C. to about 60° C. to provide compound 5b. Compound 5b can be further converted to a sulphoxide or sulphone, compound 5c, by reacting compound 5b with an oxidizing agent such as hydrogen peroxide, mCPBA, oxone and the like in an organic solvent such as acetone, acetonitrile, methanol, ethanol or the like, at a temperature from about –20° C. to about room temperature.

Scheme 2

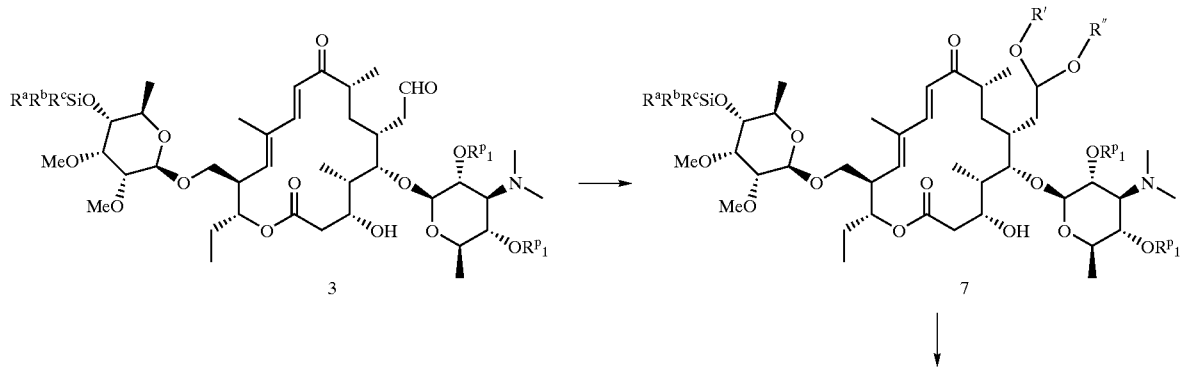

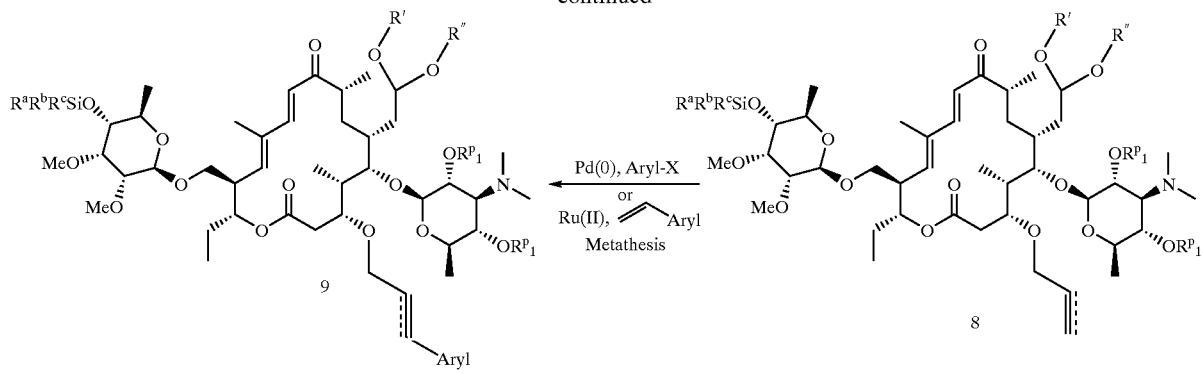

In yet another process of the invention for the preparation of the compounds of Formula I, compound 3 of Scheme 1 is treated with acetyl chloride, hydrochloric acid, acetic acid or the like to provide a pH between from about 1 to about 4 in an alcoholic solvent such as methanol, ethanol, ethylene glycol or the like to protect the aldehyde as an acetyl (compound 7). Compound 7 is reacted with an allyl bromide or propargyl bromide as described above in Scheme 1 to provide compound 8. Compound 8 is treated with an aryl halide or aryl triflate in the presence of a palladium catalyst [Pd(0) or Pd(II)] to provide compound 9: (See (a) Heck, Palladium Reagents in Organic Synthesis, Academic Press: New York, 1985, Chapter 1; (b) Sonogashira, Comprehensive Organic Synthesis, Volume 3, Chapters 2,4; (c) Sonogashira, *Synthesis* 1977, 777.). Under the Heck coupling conditions, regioisomers and stereoisomers of the double bond are possible. Alternatively, compound 8 can undergo a cross metathesis reaction with vinylaromatic derivatives using ruthenium catalysts (see (a) *J. Org. Chem.* 2000, 65, 2204–2207; (b) Reviews: *Synlett.* 1999, 2, 267; (c) Reviews: Ivin, K. J.; Mol, J. C. *Olefin Metathesis and Metathesis Polymerization*, 2$^{nd}$ ed.; Academic Press: New York, 1997; (d) *J. Org. Chem.* 1999, 64, 4798–4816; (e) *Angew. Chem., Int. Ed. Engl.* 1997, 36, 2036–2056; (f) *Tetrahedron* 1998, 54, 4413–4450). Alternatively, the propargyl group of compound 8 is reduced with a variety of borane reagents to give vinyl boronic acid further employing palladium catalyzed Suzuki coupling reactions to provide compound 9 (see (a) Suzuki, Chemical Reviews, 1995, 95, 2457; (b) Suzuki, *Pure & Appl. Chem.* 1991, 63, 419). Compound 9 is further deprotected as described earlier to provide ether compounds of Formula I.

Scheme 4

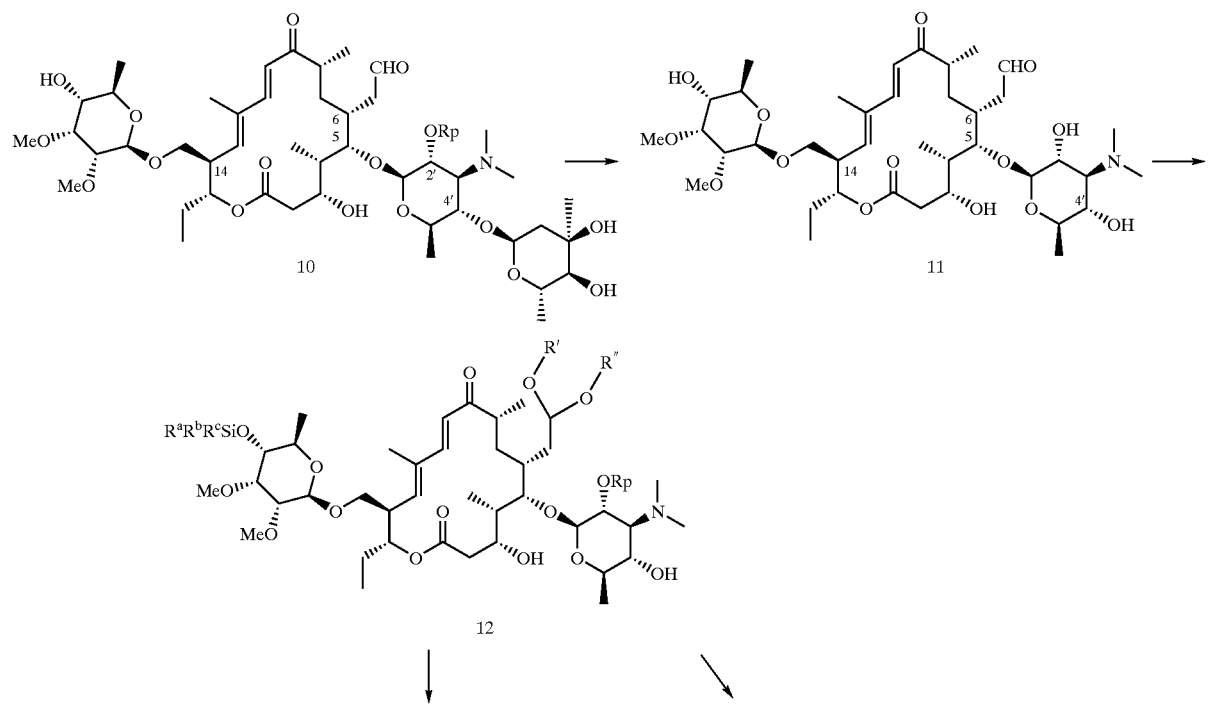

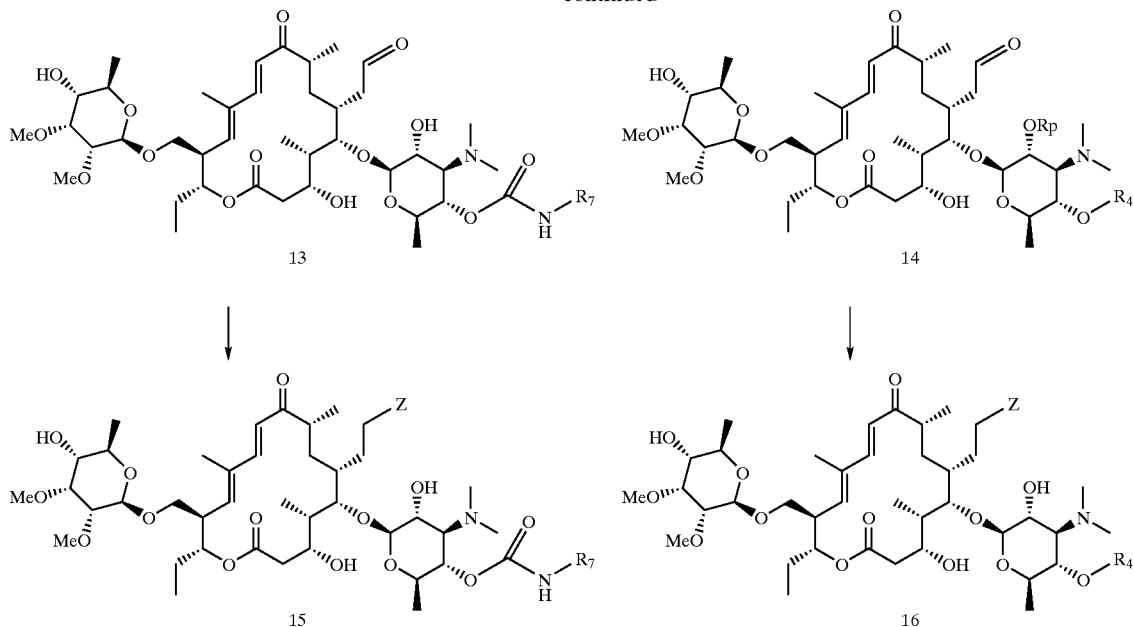

Another process of the invention for the preparation of the compounds of Formula I comprises treating 2'-protected tylosin (compound 10 of Scheme 4) with dilute aqueous acids (0.1–5N) such as hydrochloric acid, sulfuric acid, trifluoroacetic acid, acetic acid or the like or optionally in an organic solvent such as acetone, acetonitrile, methanol, ethanol or the like or combinations thereof at from about 0° C. to about 100° C. for 1–24 hours to provide compound 11. Compound 11 is treated with acetyl chloride, hydrochloric acid, acetic acid or the like to provide a pH of 1–4 in an alcoholic solvent such as methanol, ethanol, ethylene glycol or the like to provide an acetal intermediate. The acetal intermediate is further treated with a silylating agent such as triethylsilyl chloride, TBDMSCl, TBDPSCl or the like, optionally with the addition of DMAP, imidazole or the like, in an aprotic solvent such as methylene chloride, ethylene chloride, THF, chloroform, DMF, acetonitrile or the like at from about 0° C. to about 50° C. for 1–48 hours to provide compound 12. Compound 12 is alkylated with an alkylating agent such as an alkyl halide, alkyl sulphonate, propargyl halide, allyl halide, arylallyl halide, heteroarylallyl halide, benzyl halide or the like in the presence of a base such as sodium hydride, potassium hydride, potassium tert-butoxide, potassium hydroxide, KHMDS, or the like in an aprotic solvent such as THF, DMSO, DMF, dioxane, or the like or mixtures thereof at from about −20° C. to about 60° C. to provide a protected compound 14 which can be deprotected with aqueous acid to remove the acetal protecting group and TBAF or hydrofluoric acid to remove the silyl protecting group followed by methanolysis at temperature(s) between room temperature to reflux temperature to remove the $R^P$ protecting group at the 2'-position where $OR^P$ is an ester or a silyl ether to provide compound 14. Compound 12 can also be treated with an isocyanate reagent in an aprotic solvent such as methylene chloride, ethylene chloride, THF, chloroform, DMF, acetonitrile or the like at from about 0° C. to about 50° C. for 1–48 hours followed by deprotection of the protecting groups to provide compound 13. Compound 13 and 14 can also be further reduced to a corresponding alcohol with various hydride reducing agents such as sodium borohydrides, lithium borohydrides or the like in an organic solvent such as methanol, ethanol, isopropanol, acetonitrile, THF or the like. The alcohol compound can be converted to an ether compound of the invention by treatment with an alkyl halide, alkyl sulphonate, propargyl halide, allyl halide, arylallyl halide, heteroarylallyl halide, benzyl halide or the like in the presence of a base such as sodium hydride, potassium hydride, potassium tert-butoxide, potassium hydroxide, KHMDS, or the like in an aprotic solvent such as THF, DMSO, DMF, dioxane, or the like or mixtures there of at from−20° C. to 60° C. to provide compound 15 or 16 where Z is O—M—Y where M, Y, R4 and R7 are previously defined in formula I. Compound 13 and 14 can be further derivatized to an amino derivative via reductive amination methods by treating with an amine compound in the presence of sodium borohydride, sodium cyanoborohydride or the like in an alcoholic solvent such as methanol, ethanol or isopropanol or in acetonitrile or the like at a pH of 2–6 to provide compound 15 and 16 where Z is NR8R9 where R4, R7, R8, and R9 are previously defined in Formula I.

EXAMPLES

The procedures described above for preparing the compounds of Formula I of the present invention will be better understood in connection with the following examples which are intended to be illustrative only of, and not limiting of the scope of the invention. Various changes and modifications to the disclosed embodiments will be apparent to those skilled in the art. Such changes and modifications, including without limitation, those relating to the chemical structures, substituents, derivatives, syntheses, formulations and/or methods of the invention may be made without departing from the spirit of the invention and the scope of the appended claims.

Example 1

Compound of Formula I: Z=—OCH$_2$CHCH$_2$, R1 and R2 taken together=O, R3=H, R$_{p1}$=H, R$^P_2$=H and R4=H Step 1a. Compound 2 of Scheme 1 where R$^P_1$=acetyl Tylosin (205 g, 0.22 mole) was added to 1 N aqueous HCl (500 mL). The resulting mixture was stirred for 3 hours at room temperature. The reaction mixture was neutralized with concentrated NH$_4$OH and extracted with CHCl$_3$ (3×500 mL). The combined organic fractions were washed with water (2×500 mL), dried (Na$_2$SO$_4$), filtered and concentrated under reduced pressure. The crude residue was dissolved in acetone (800 mL) followed by the addition of acetic anhydride (200 mL) at room temperature. The resulting mixture was stirred for 4 hours. The solvent and the excess reagent were removed under reduced pressure. The residue was dissolved in toluene (100 mL) and the solvent was removed under reduced pressure (this procedure was repeated 3 times) to give 191 g (100%) of the title compound as a yellow foamy solid.

MS (ESI) m/z 856 (M+H)$^+$.

Step 1b. Compound 3 of Scheme 1 where R$^a$R$^b$R$^c$Si=trimethylsilyl and R$^P_1$=acetyl Imidazole (9.2 g, 0.135 mole) was added to a solution of the compound from step 1a (105 g, 0.12 mole) in dry DMF (400 mL) at room temperature. The resulting mixture was stirred until all the imidazole was dissolved. TBDMSCl (19.4 g, 0.128 mole) was added to this solution in one portion. The reaction mixture was stirred at room temperature for 15 hours. Additional imidazole (10 g, 0.147 mole) and TBDMSCl (10 g, 0.066 mole) were added to the reaction. After 3 days the reaction mixture was diluted with EtOAc, washed with saturated NaHCO$_3$ (2×500 mL), water (4×500 mL), brine (1×500 mL), dried (Na$_2$SO$_4$) and concentrated under reduced pressure to give 121 g of the crude title compound. Purification of 10 g of the crude mixture by flash chromatography on silica gel (hexane:acetone/5:1) gave 5.1 g (60% for three steps) of the title compound.

MS (ESI) m/z 970 (M+H)$^+$. $^{13}$C NMR (100 MHz, CDCl$_3$): 205.0, 175.6, 171.7, 171.2, 150.0, 144.2, 136.6, 120.0, 103.7, 103.0, 83.0, 82.9, 82.7, 77.1, 77.0, 73.3, 73.0, 72.4, 71.4, 70.7, 69.0, 68.6, 63.6, 61.5, 47.0, 46.9, 45.5, 43.1, 42.7, 41.2, 36.6, 33.6, 33.5, 33.0, 27.7, 27.2, 24.5, 23.2, 23.1, 20.0, 19.8, 19.4, 19.1, 16.0, 15.0, 11.6, 10.5, -2.0, -3.0.

Step 1c. Compound 5 of Scheme 1 where R$^a$R$^b$R$^c$Si=trimethylsilyl and R$^P_1$=acetyl To a solution of the compound from step 1b (4.57 g, 4.7 mmol) in isopropanol (47 mL, 0.1 M) cooled to 0° C., NaBH$_4$ (44.6 mg, 1.2 mmol) was added in three portions in 10 minute intervals. The resulting mixture was stirred at 0° C. for 45 min. The reaction mixture was treated with water (50 mL) and 2% solution of tris (hydroxymethyl)aminomethane (15 mL) and stirred for 20–30 minutes keeping the reaction at 0° C. The reaction mixture was diluted with EtOAc (300 mL). The organic phase was separated and washed with water (300 mL), saturated NaHCO$_3$ (300 mL), brine (300 mL) and dried (Na$_2$SO$_4$). Evaporation of the solvent under reduced pressure gave 4.6 g (100%) of the title compound as a white foamy solid.

MS (ESI) m/z 972 (M+H)$^+$. $^{13}$C NMR (100 MHz, CDCl$_3$): 205.7, 175.9, 171.5, 171.1, 149.7, 143.7, 136.7, 120.3, 104.1, 103.0, 83.1, 82.9, 82.8, 77.0, 73.3, 72.7, 72.4, 71.3, 70.5, 69.1, 64.0, 63.5, 62.7, 61.4, 46.8, 46.6, 43.0, 42.4, 41.0, 36.5, 33.4, 33.2, 27.6, 27.1, 27.0, 24.4, 23.1, 23.0, 22.5, 19.8, 19.7, 19.4, 19.0, 15.9, 14.9, 11.4, 10.8, -2.1, -3.0.

Step 1d. Compound of Formula I: Z=—OCH$_2$CHCH$_2$, R1 and R2 taken together=O, R3=H, R$^P_1$=acetyl, R$^P_2$=TBDMS and R4=acetyl A flask containing a solution of the compound of step 1c (1.5 g, 1.54 mmol) in dry THF (25 mL, 0.06 M) was flashed with N$_2$ and then degassed under vacuum at-78° C. by freeze-thaw cycle (3 cycles). The flask was warmed up to room temperature. Keeping the solution under inert atmosphere, Pd$_2$(dba)$_3$ (141 mg, 0.154 mmol) and dppb (132 mg, 0.308 mmol) were added in one portion quickly one after another, followed by the addition of CH$_2$CHCH$_2$OCO$_2$t-Bu (317 mg, 2 mmol). The resulting mixture was stirred at room temperature for about two minutes. The flask was equipped with a reflux condenser and the reaction mixture was heated in a 69–71° C. oil bath for 5 hours. The reaction mixture was cooled to 20° C., diluted with EtOAc (10 mL) and stirred for 30 minutes. The solution was filtered through celite, diluted with more EtOAc (100 mL), washed with saturated NaHCO$_3$ (50 mL), brine (50 mL) and dried (Na$_2$SO$_4$). Evaporation of the solvent gave 1.7 g of the crude product as a dark orange solid. Purification on silica gel by gradient of solvent mixture (hexanes:acetone/9:1, then 6:1) gave 950 mg (60%) of the title compound as a white solid.

MS (ESI) m/z 1012 (M+H)$^+$. $^{13}$C NMR (100 MHz, CDCl$_3$): 205.6, 175.8, 171.6, 171.2, 149.4, 143.6, 137.0, 136.7, 120.5, 118.26, 104.0, 103.0, 83.0, 82.8, 82.6, 77.1, 73.5, 73.1, 72.8, 72.5, 73.3, 70.8, 70.3, 69.2, 63.6, 61.4, 46.8, 43.1, 42.8, 41.5, 35.1, 29.9, 27.7, 27.1, 23.2, 23.1, 19.7, 19.6, 19.1, 14.9, 11.6, 10.7.

Step 1e. Compound of Formula I: Z=—OCH2CHCH$_2$, R1 and R2 taken together=O, R3=H, R$^P_1$=acetyl, R$^P_2$=H and R4=acetyl A solution of tert-butyl ammonium fluoride (TBAF) in THF (1.65 mL, 1 M, 5 eq) was added drop wise to a solution of the compound from step 1d (330 mg, 0.33 mmol) in dry THF (2 mL) at 0° C. The resulting mixture was stirred for 30 minutes at 0° C. The reaction mixture was diluted with EtOAc (25 mL), washed with NaHCO$_3$ (2×25 mL), brine (25 mL) and dried (Na$_2$SO$_4$). Purification by flash chromatography on silica gel gave 150 mg (50%) of the title compound.

MS (ESI) m/z 898 (M+H)$^+$.

Step 1f. Compound of Formula I; Z=—OCH$_2$CHCH$_2$, R1 and R2 taken together=O, R3=H, R$^P_1$=H, R$^P_2$=H and R4=H A solution of the compound from step 1e (33 mg) in methanol (3 mL) was stirred for 12 hours at room temperature. The solvent was evaporated under reduced pressure. The solution of the crude mixture in acetone was filtered through a short layer of silica gel to give 23 mg (79%) of the title compound as a white solid.

MS (ESI) m/z 814 (M+H)$^+$.

Example 2

Compound of Formula I: Z=—OCHCHCH-phenyl, R1 and R2 taken together=O, R3=H, R$^P_1$=H, R$^P_2$=H and R4=H Step 2a. Compound of Formula I: Z=—OCH$_2$CHCH-phenyl, R1 and R2 taken together=O, R3=H, R$^P_1$=acetyl, R$^P_2$=TBDMS and R4=acetyl Bis(tricyclohexylphosphine) benzylidene ruthenium(iv) dichloride (Grubbs' catalyst) (48 mg, 0.059 mmol) was added in one portion to a solution of styrene (204 μL, 1.8 mmol) and the compound from step 1d of example 1 (600 mg, 0.59 mmol) in CH$_2$Cl$_2$ (3 mL) at room temperature. The resulting mixture was refluxed for 2.5 hours, cooled to room temperature, diluted with CH$_2$Cl$_2$ (50 mL) washed with saturated NaHCO$_3$ solution (2×50 mL), brine (50 mL), dried (Na$_2$SO$_4$) and evaporated. Purification on silica gel (hexanes/acetone:7/1) gave 430 mg (67%) of the title compound.

MS (ESI) m/z 1088 (M+H)$^+$. $^{13}$C NMR (100 MHz, CDCl$_3$): 205.6, 175.8, 171.6, 171.2, 149.5, 143.7, 139.1, 136.8, 133.4, 130.9, 130.4, 130.1, 129.2, 128.7, 128.6, 104.0, 103.1, 83.0, 82.9, 82.7, 77.1, 73.5, 72.8, 72.7, 72.6, 71.4, 71.0, 70.3, 69.2, 63.6, 61.4, 46.8, 43.1, 42.8, 41.5, 32.8, 31.2, 29.9, 27.7, 27.2, 23.3, 23.1, 19.9, 19.8, 17.2, 14.9, 11.6, 10.7, –2.0, –2.9.

Step 2b. Compound of Formula I: Z=—OCH$_2$CHCH-phenyl, R1 and R2 taken together=O, R3=H, R$^P_1$=acetyl, R$^P_2$=H and R4=acetyl A solution of TBAF in THF (1.3 mL, 1 M, 5 eq) was added dropwise to a solution of the compound from step 2a (290 mg, 0.27 mmol) in dry THF (3 mL, 0.09 M) at 0° C. The resulting mixture was stirred for 1 hour at 0° C. The reaction mixture was diluted with EtOAc (50 mL), washed with NaHCO$_3$ (3×50 mL), brine (50 mL) and dried (Na$_2$SO$_4$). Purification by flash chromatography on deactivated with 20% of H$_2$O silica gel (hexane/acetone:5/1, then 2/1 gave 245 mg (94%) of the title compound.

MS (ESI) m/z 974 (M+H)$^+$.

Step 2c. Compound of Formula I: Z=—OCH$_2$CHCH-phenyl, R1 and R2 taken together=O, R3=H, R$^P_1$=H, R$^P_2$=H and R4=H A solution of the compound from step 2b (245 mg) in methanol (5 mL) was stirred for 12 hours at room temperature. The solvent was removed under reduced pressure to give 226 mg of the crude product. Purificatin by flash chromatography on silica gel (hexane/acetone: 1/1) gave 110 mg (50%) of the title compound as a white solid.

MS (ESI) m/z 890 (M+H)$^+$. $^{13}$C NMR (100 MHz, CDCl$_3$) partial data: 205.8, 175.8, 149.8, 143.8, 139.3, 136.8, 133.8, 130.5, 130.4, 128.6, 127.5, 105.8, 103.0, 83.8, 81.8, 74.6, 72.5, 63.7, 61.6, 43.7, 19.7, 14.9, 11.6.

Example 3

Compound of Formula I: Z=—OC(O)CH$_2$-(4-chlorophenyl), R1 and R2 taken together O, R3=H, R$^P_1$=H, R$^P_2$=H and R4=H Step 3a. Compound of Formula I: Z=—OC(O)CH$_2$-(4-chlorophenyl), R1 and R2 taken together=O, R3=H, R$^P_1$=acetyl, R$^P_2$=TBDMS and R4=acetyl To a solution of chlorophenylacetic acid (35 mg, 0.2 mmol) in dry CH$_2$Cl$_2$ (2 mL) DCC (44.6 mg, 0.215 mmol) was added at room temperature. The resulting mixture was stirred for 5 minutes. A solution of the compound from step 1c of example 1 (200 mg, 0.2 mmol) in CH$_2$Cl$_2$ (1 mL) was added to the reaction mixture followed by the addition of a catalytic amount of DMAP. After 10 minutes the reaction mixture was filtered through a short layer of celite and solvent was removed under reduced pressure. Purification of the crude mixture by flash chromatography on silica gel (hexane/acetone:6/1) gave 180 mg (78%) of the title compound as a white solid.

MS (ESI) m/z 1124 (M+H)$^+$.

Step 3b. Compound of Formula I: Z=—OC(O)CH$_2$-(4-chlorophenyl), R1 and R2 taken together=O, R3=H, R$^P_1$=acetyl, R$^P_2$=H and R4=acetyl A solution of TBAF in THF (0.6 mL, 1 M, 4 eq) was added dropwise to a solution of the compound from step 3a (180 mg, 0.16 mmol) in dry THF (2 mL) at 0° C. The resulting mixture was stirred for 1 hour at 0° C. The reaction mixture was diluted with EtOAc (25 mL), washed with NaHCO$_3$ (2×25 mL), brine (25 mL) and dried (Na$_2$SO$_4$). Filtration through a short silica gel column (hexane/acetone:3/1) gave 150 mg (93%) of the title compound.

MS (ESI) m/z 1010 (M+H)$^+$.

Step 3c. Compound of Formula I: Z=—OC(O)CH$_2$-(4-chlorophenyl), R1 and R2 taken together=O, R3=H, R$^P_1$=H, R$^P_2$=H and R4=H A solution of the compound from step 3b (150 mg) in methanol (3 mL) was heated at 45° C. for 3 hours. The solvent was removed under reduced pressure. Purification by flash chromatography (hexanes/acetone:1/1) gave 85 mg (62%) of the title compound as a white solid.

MS (ESI) m/z 926 (M+H)$^+$.

Example 4

Compound of Formula I: Z=—NHCH$_2$C≡C-(3-quinolyl), R1 and R2 taken together=O, R3=H, R$_{p1}$=H, R$^P_2$=H and R4=H Step 4a. Compound of Formula I: Z=—NHCH$_2$C≡CH, R1 and R2 taken together=O, R3=H, R$^P_1$=acetyl, R$^P_2$=H and R4=acetyl To a solution of the compound from step 1a from example 1 (1.1 g, 1.3 mmol) in CH$_3$CN (6.5 mL), a 0.5 M solution of NaH$_2$PO$_4$ (3 mL) was added followed by the addition of propargyl amine (106 µL, 1.5 mmol) at 0° C. The pH of the solution was adjusted to 5–6 by the careful addition of 1N HCl. NaCNBH$_3$ (121 mg, 1.9 mmol) was added to the resulting solution and the reaction mixture was left to warm to room temperature for 30 minutes. The reaction mixture was diluted with water (50 mL) and extracted with CH$_2$Cl$_2$ (2×100 mL). The combined organic phases were washed with saturated NaHCO$_3$ (2×100 mL), brine (100 mL) and dried (Na$_2$SO$_4$). Removal of the solvent under reduced pressure gave 1.06 g (92%) of the crude title compound. The crude product was used in the next step without further purification.

MS (ESI) m/z 895 (M+H)$^+$.

Step 4b. Compound of Formula I: Z=—NHCH$_2$C≡C-(3-quinolyl), R1 and R2 taken together=O, R3=H, R$^P_1$=acetyl, R$^P_2$=H and R4=acetyl To a solution of the compound from step 4a (600 mg, 0.67 mmol) in CH$_3$CN (6 mL, 0.1 M) and Et$_3$N (1.5 mL) in a sealed tube, 3-bromoquinoline (109 µL, 0.8 mmol) was added at room temperature. The solution was degassed under vacuum at–78° C. by freeze-thaw cycle (3 cycles). Keeping the reaction mixture under N$_2$, PdCl$_2$(Ph$_3$P)$_2$ (47 mg, 0.067 mmol) and CuI (6.4 mg, 0.034 mmol, 5%) were added and the resulting mixture was stirred for 5 minutes at room temperature. The reaction mixture was warmed in an oil bath from 30° C. to 70° C. for 30 minutes and then kept at 70° C. in an oil bath for 4.5 hours. The reaction mixture was diluted with EtOAc (50 mL) and stirred at room temperature. The organic phase was washed with saturated NaHCO$_3$ (2×50 mL), brine (50 mL) and dried (Na$_2$SO$_4$). The solvent was removed under reduced pressure giving the crude mixture which was purified by flash chromatography (CH$_2$Cl$_2$/MeOH (2M NH$_3$):20/1) to give 220 mg of the title compound, containing another isomer with the same mass.

MS (ESI) m/z 1022 (M+H)$^+$.

Step 4c. Compound of Formula I: Z=—NHCH$_2$C≡C-(3-quinolyl), R1 and R2 taken together=O, R3=H, R$^P_1$=H, R$^P_2$=H and R4=H A solution of the compound from step 4b (220 mg) in methanol (5 mL) was heated at 50° C. for 1.5 hours and stirred at room temperature for 12 hours. The solvent was removed under reduced pressure. Purification on silica gel by flash chromatography (CH$_2$Cl$_2$/MeOH (2M NH$_3$):15/1) gave 43 mg (%) of the title compound as a white solid and 90 mg (%) of a mixture of isomers.

MS (ESI) m/z 937 (M+H)$^+$.

Example 5

Compound of Formula I: Z=—N(CH$_3$)CH$_2$C≡C-(3-quinolyl), R1 and R2 taken together O, R3=H, R$^P_1$=H, R$^P_2$=H and R4=H To a solution of the mixture of compounds from step 4c of Example 4 (90 mg, 0.096 mmol) in MeOH (3 mL), a 37% solution of formaldehyde in water (150 μL, 6 eq) was added in one portion at 0° C. The pH of the solution was adjusted to 5–6 by the careful addition of AcOH (consumed 150 μL). NaCNBH$_3$ (25 mg, 0.42 mmol) was added to the resulting solution and the reaction mixture was stirred for 30 minutes at 0° C. The reaction mixture was diluted with water (20 mL) and extracted with EtOAc (2×30 mL). The combined organic phases were washed with saturated NaHCO$_3$ (2×30 mL), brine (30 mL) and dried (Na$_2$SO$_4$). Removal of the solvent under reduced pressure gave 100 mg of the crude title compound. Purification by flash chromatography (CH$_2$Cl$_2$/MeOH (2M NH$_3$): 15/1) gave 75 mg (82%) of the title compound.

MS (ESI) m/z 952 (M+H)$^+$.

Example 6

Compound of Formula I: Z=—NHCH$_2$C≡CH, R1 and R2 taken together=O, R3=H, $R^P_1$=H, $R^P_2$=H and R4=H A solution of the compound from step 4a is treated with methanol at reflux to give the title compound.

Example 7

Compound of Formula I: Z=—OCH$_2$CH=CH-phenyl, R1 and R2 taken together=O, R3=H, R4=—CH$_2$C≡CH, $R^P_1$=H, and $R^P_2$=H Step 7a. Compound of Formula I: Z=—OCH$_2$CH=CH-phenyl, R1 and R2 taken together=O, R3=H, R4=H, $R^P_1$=H, and $R^P_2$=TBDMS Compound from step 1d of Example 1 is treated with methanol at room temperature for 24 hours and removal of the solvent in vacuo provided the title compound.

Step 7b. Compound of Formula I: Z=—OCH$_2$CH=CH-phenyl, R1 and R2 taken together=O, R3=H, R4=—CH$_2$C≡CH, $R^P_1$=H, and $R^P_2$=TBDMS Compound from step 7a is stirred with 2N aqueous NaOH, propargyl bromide (2 equivalents) and n-tetrabutyl ammonium bromide in dichloromethane at room temperature for 10 hours. The mixture is taken up in dichloromethane and is washed with water, brine and dried over Na$_2$SO$_4$. Removal of the solvent and purification on silica gel column provides the title compound.

Step 7c. Compound of Formula I: Z=—OCH$_2$CH=CH-phenyl, R1 and R2 taken together=O, R3=H, R4=—CH$_2$C≡CH, $R^P_1$=H, and $R^P_2$=H Compound of step 7b is treated according to the procedure of step 1f of Example 1 to provide the title compound of Example 7.

Example 8

Compound of Formula I: A=—CH$_2$OCH$_2$CH=CH-phenyl, R1 and R2 taken together=O, R3=H, R4=—CH$_2$C≡C-(2-pyridyl), $R^P_1$=H, and $R^P_2$=H Compound of Example 7 is treated according to the procedure of step 4d substituting 2-bromopyridyl for 3-bromoquinolyl to provide the title compound.

Example 9

Compound of Formula I: Z=—OCH$_2$CH=CH-phenyl, R1 and R2 taken together=O, R3=H, R4=—CH$_2$C≡C-(3-quinolyl), $R^P_1$=H, and $R^P_2$=H Compound of Example 7 is treated according to the procedure of step 4b of Example 4 to provide the title compound.

Example 10

Compound of Formula I: Z=—OCH$_2$CH=CH-phenyl, R1 and R2 taken together=O, R3=—CH$_3$, R4=H, $R^P_1$=H, and $R^P_2$=H Step 10a. Compound of Formula I: Z=—OCH$_2$CH=CH-phenyl, R1 and R2 taken together=O, R3=—CH$_3$, R4=acetyl, $R^P_1$=acetyl, and $R^P_2$=TBDMS Compound from step 2a of Example 2 is stirred with 2N aqueous NaOH, methyl iodide (2 equivalents) and n-tetrabutyl ammonium bromide in dichloromethane at room temperature for 24 hours. The mixture is taken up in dichloromethane and is washed with water, brine and dried over Na$_2$SO$_4$. Removal of the solvent and purification on silica gel column provides the title compound.

Step 10b. Compound of Formula I: Z=—OCH$_2$CH=CH-phenyl, R1 and R2 taken together=O, R3=—CH$_3$, R$_4$=acetyl, $R^P_1$=acetyl, and $R^P_2$=H Compound of step 10a is treated according to the procedure of step 1e of Example 1 to provide the title compound.

Step 10c. Compound of Formula I: Z=—OCH$_2$CH=CH-phenyl, R1 and R2 taken together=O, R3=—CH$_3$, R4=H, $R^P_1$=H, and $R^P_2$=H Compound of step 10b is treated with methanol at room temperature for 24 hours and removal of the solvent provides the title compound of Example 10.

Example 11

Compound of Formula I: Z=—OCH$_2$CH=CH-phenyl, R1 and R2 taken together=O, R3=—CH$_3$, R4=—CH$_2$CH=CH$_2$, $R^P_1$=H, and $R^P_2$=H Step 11a. Compound of Formula I: Z=—OCH$_2$CH=CH-phenyl, R1 and R2 taken together O, R3=—CH$_3$, R4=H, $R^P_1$=H, and $R^P_2$=TBDMS Compound of step 10a of Example 10 is treated with methanol at room temperature for 24 hours and removal of the solvent provides the title compound.

Step 11b. Compound of Formula I: Z=—OCH$_2$CH=CH-phenyl, R1 and R2 taken together=O, R3=—CH$_3$, R4=—CH$_2$CH=CH$_2$ $R^P_1$=H, and $R^P_2$=TBDMS Compound of step 11a is treated with allyl tert-butyl carbonate (2 equivalents) and Pd(PPh$_3$)$_4$ (10%) in dried THF and is heated at 65–70° C. for 4–8 hours. The crude reaction mixture is taken up in ethyl acetate and is washed with water, brine and is dried over Na$_2$SO$_4$. Removal of the solvents and column chromatography on silica gel column provides the title compound.

Step 11c. Compound of Formula I: Z=—OCH$_2$CH=CH-phenyl, R1 and R2 taken together=O, R3=—CH$_3$, R4=—CH$_2$CH=CH$_2$, $R^P_1$=H, and $R^P_2$=H Compound of step 11b is treated according to the procedure of step 1e of Example 1 to provide the title compound of Example 11.

Example 12

Compound of Formula I: Z=—OCH$_2$CH=CH-phenyl, R1 and R2 taken together=O, R3=—CH$_3$, R4=—CH$_2$CH=CH-(3-pyridyl), $R^P_1$=H, and $R^P_2$=H Compound of Example 11 is treated with (Ph$_3$P)$_2$PdCl$_2$ (10%), triethylamine (3 equivalents), and 3-bromopyridine in toluene and is heated at 100° C. for 12–24 hours. Removal of the solvent in vacuo and purification on silica gel column provide the title compound.

Example 13

Compound of Formula I: Z=—OC(O)CH$_2$-(4-chlorophenyl), R1 and R2 taken together=O, R3=H, R4=—CH$_2$CH=CH$_2$, $R^P_1$=H, and $R^P_2$=H Compound of step 3a of Example 3 is treated according to the procedures of steps 11a to 11c of Example 11 to provide the title compound.

Example 14

Compound of Formula I: Z=—OC(O)CH$_2$-(4-chlorophenyl), R1 and R2 taken together=O, R3=H, R4=—CH$_2$CH=CH-(3-pyridyl), R$^P_1$=H, and R$^P_2$=H Compound of Example 13 is treated with (Ph$_3$P)$_2$PdCl$_2$ (10%), triethylamine (3 equivalents), and 3-bromopyridine in toluene and is heated at 100° C. for 12–24 hours. Removal of the solvent in vacuo and purification on silica gel column provides the title compound of Example 14.

Example 15

Compound of Formula I: Z=—N(CH$_3$)CH$_2$C≡C-(3-quinolyl), R1 and R2 taken together=O, R3=—CH$_3$, R4=H, R$^P_1$=H, and R$^P_2$=H Step 15a. Compound of Formula I: Z=—N(CH$_3$)CH$_2$C≡C-(3-quinolyl), R1 and R2 taken together=O, R3=H, R4=TES, R$^P_1$=TES, and R$^P_2$=TES Compound of Example 5 is treated with triethylsilyl chloride (3.5 equivalents) and triethyl amine in dichloromethane at room temperature for 24 hours. The reaction mixture is taken up in ethyl acetate and is washed with water, brine and dried over Na$_2$SO$_4$. Removal of the solvent in vacuo and purification on silica gel column provides the title compound.

Step 15b. Compound of Formula I: Z=—N(CH$_3$)CH$_2$C≡C-(3-quinolyl), R1 and R2 taken together=O, R3=—CH$_3$, R4=TES, R$^P_1$=TES, and R$^P_2$=TES Compound of step 15a is treated according to procedure of step 10a of Example 10 provides the title compound.

Step 15c. Compound of Formula I: Z=—N(CH$_3$)CH$_2$C≡C-(3-quinolyl), R1 and R2 taken together=O, R3=—CH$_3$, R4=H, R$^P_1$=H, and R$^P_2$=H Compound of step 15b is treated with TBAF (5–6 equivalents) in THF at room temperature for 4–8 hours. The mixture is taken up in ethyl acetate and is washed with water, brine and dried over Na$_2$SO$_4$. Removal of the solvent in vacuo and purification on silica gel column provides the title compound of Example 15.

Although the invention has been described with respect to various preferred embodiments, it is not intended to be limited thereto, but rather those skilled in the art will recognize that variations and modifications may be made therein which are within the spirit of the invention and the scope of the appended claims.

What is claimed is:

1. A compound represented by Formula I, or a pharmaceutically acceptable salt, ester or prodrug thereof, where Formula I is:

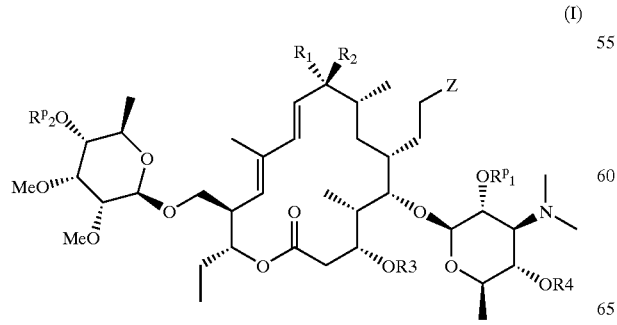

(I)

In Formula I:
Z is selected from the group consisting of:
(1) —NR7R8, wherein R7 and R8 are each independently selected from hydrogen, C1–C6-alkyl, optionally substituted with one or more substituents selected from the group consisting of halogen, aryl, substituted aryl, heterocyclic and substituted heterocyclic, C2–C6-alkenyl, optionally substituted with one or more substituents selected from the group consisting of halogen, aryl, substituted aryl, heterocyclic and substituted heterocyclic, C2–C6-alkynyl, optionally substituted with one or more substituents selected from the group consisting of halogen, aryl, substituted aryl, heterocyclic and substituted heterocyclic or R7R8 taken with the nitrogen atom to which they are connected form a 3- to 7-membered ring which may optionally contain a hetero function selected from the group consisting of —O—, —NH—, —N(C1–C6-alkyl)-, —N(aryl)-, —N(heteroaryl)-, —S—, —S(O)— and —S(O)$_2$—;

(2) —NR7C(O)—R9, where R7 is as previously defined and R9 is selected from the group consisting of:
  (a) C1–C6-alkyl, optionally substituted with one or more substituents selected from the group consisting of halogen, aryl, substituted aryl, heterocyclic and substituted heterocyclic;
  (b) C2–C6-alkenyl, optionally substituted with one or more substituents selected from the group consisting of halogen, aryl, substituted aryl, heterocyclic and substituted heterocyclic;
  (c) C2–C6-alkynyl, optionally substituted with one or more substituents selected from the group consisting of halogen, aryl, substituted aryl, heterocyclic and substituted heterocyclic;
  (d) aryl;
  (e) substituted aryl;
  (f) heterocyclic; and
  (g) substituted heterocyclic;

(3) —NR7C(O)—NR8R9, where R7, R8, and R9 are as previously defined;

(4) —S(O)$_n$—R10, where R10 is selected from the group consisting of aryl, substituted aryl, heterocyclic and substituted heterocyclic and where n=0, 1 or 2;

(5) —S(O)$_n$—(C1–C6-alkyl), optionally substituted with one or more substituents selected from the group consisting of halogen, aryl, substituted aryl, heterocyclic and substituted heterocyclic, where n is as previously defined;

(6) —S(O)$_n$—(C2–C6-alkenyl), optionally substituted with one or more substituents selected from the group consisting of halogen, aryl, substituted aryl, heterocyclic and substituted heterocyclic, where n is as previously defined;

(7) —S(O)$_n$—(C2–C6-alkynyl), optionally substituted with one or more substituents selected from the group consisting of halogen, aryl, substituted aryl, heterocyclic and substituted heterocyclic, where n is as previously defined; and (8) —O—M—Y, where M is:
  (a) absent,
  (b) —C(O)—
  (c) —C(O)N(R7)-, where R7 is as previously defined,
  (d) —C1–C6-alkyl-N(R7)-, where R7 is as previously defined, (e) —C2–C6-alkenyl-N(R7)-, where R7 is as previously defined, or (f) —C2–C6-alkynyl-N(R7)-, where R7 is as previously defined;

and where Y is:
(a) hydrogen,
(b) hydroxy protecting group,
(c) C1–C6-alkyl, optionally substituted with one or more substituents selected from the group consisting of halogen, aryl, substituted aryl, heterocyclic and substituted heterocyclic,
(d) C2–C6-alkenyl, optionally substituted with one or more substituents selected from the group consisting of halogen, aryl, substituted aryl, heterocyclic and substituted heterocyclic,
(e) C2–C6-alkynyl, optionally substituted with one or more substituents selected from the group consisting of halogen, aryl, substituted aryl, heterocyclic and substituted heterocyclic,
(f) aryl,
(g) substituted aryl,
(h) heterocyclic, or
(i) substituted heterocyclic;

R1 and R2 are each independently selected from the group consisting of:
(a) hydrogen;
(b) hydroxy;
(c) protected hydroxy;
(d) OC(O)—C1–C12-alkyl, optionally substituted with one or more substituents selected from the group consisting of halogen, aryl, substituted aryl, heterocyclic, substituted heterocyclic, O—R7 and NR7R8 where R7 and R8 are as previously defined;
(e) O—R7, where R7 is as previously defined;
(f) halogen;
(g) R1 and R2 taken together are oxo; and
(h) NR7R8, where R7 and R8 are as previously defined;

R3 is selected from the group consisting of:
(1) hydrogen;
(2) a hydroxy protecting group;
(3) —C(O)—C1–C12-alkyl, optionally substituted with one or more substituents selected from the group consisting of halogen, aryl, substituted aryl, heterocyclic, substituted heterocyclic, O—R7 and NR7R8 where R7 and R8 are as previously defined;
(4) C1–C6-alkyl, optionally substituted with one or more substituents selected from the group consisting of halogen, aryl, substituted aryl, heterocyclic, substituted heterocyclic, O—R7 and NR7R8 where R7 and R8 are as previously defined;
(5) C2–C6-alkenyl, optionally substituted with one or more substituents selected from the group consisting of halogen, aryl, substituted aryl, heterocyclic, substituted heterocyclic, O—R7 and NR7R8 where R7 and R8 are as previously defined; and
(6) C2–C6-alkynyl, optionally substituted with one or more substituents selected from the group consisting of halogen, aryl, substituted aryl, heterocyclic, substituted heterocyclic, O—R7 and NR7R8 where R7 and R8 are as previously defined;

R4 is -D-E;
where D is:
(a) absent,
(b) —C(O)N(R7)-, where R7 is as previously defined,
(c) —C1–C6-alkyl-N(R7)-, where R7 is as previously defined,
(d) —C2–C6-alkenyl-N(R7)-, where R7 is as previously defined, or
(e) —C2–C6-alkynyl-N(R7)-, where R7 is as previously defined;

and where E is:
(a) hydrogen,
(b) C1–C6-alkyl, optionally substituted with one or more substituents selected from the group consisting of halogen, aryl, substituted aryl, heterocyclic and substituted heterocyclic,
(c) C2–C6-alkenyl, optionally substituted with one or more substituents selected from the group consisting of halogen, aryl, substituted aryl, heterocyclic and substituted heterocyclic,
(d) C2–C6-alkynyl, optionally substituted with one or more substituents selected from the group consisting of halogen, aryl, substituted aryl, heterocyclic and substituted heterocyclic,
(e) aryl,
(f) substituted aryl,
(g) heterocyclic, or
(h) substituted heterocyclic;
provided that when D is absent E is not hydrogen; and $R^P_1$ and $R^P_2$ are each independently hydrogen or a hydroxy protecting group.

2. A compound as in claim 1, where R3 is selected from the group consisting of:
(1) C1–C6-alkyl, optionally substituted with one or more substituents selected from the group consisting of halogen, aryl, substituted aryl, heterocyclic, substituted heterocyclic, O—R7 and NR7R8 where R7 and R8 are as previously defined;
(2) C2–C6-alkenyl, optionally substituted with one or more substituents selected from the group consisting of halogen, aryl, substituted aryl, heterocyclic, substituted heterocyclic, O—R7 and NR7R8 where R7 and R8 are as previously defined; and
(3) C2–C6-alkynyl, optionally substituted with one or more substituents selected from the group consisting of halogen, aryl, substituted aryl, heterocyclic, substituted heterocyclic, O—R7 and NR7R8 where R7 and R8 are as previously defined.

3. A compound as defined in claim 1 which is selected from the group consisting of:
Compound of Formula I: Z=—OCH$_2$CH=CH-phenyl, R1 and R2 taken together=O, R3=H, R4=—CH$_2$C≡CH, $R^P_1$=H and $R^P_2$=H;
Compound of Formula I: Z=—OCH$_2$CH=CH-phenyl, R1 and R2 taken together=O, R3=H, R4=—CH$_2$C≡C-(2-pyridyl), $R^P_1$=H and $R^P_2$=H;
Compound of Formula I: Z=—OCH$_2$CH=CH-phenyl, R1 and R2 taken together=O, R3=H, R4=—CH$_2$C≡C-(3-quinolyl), $R^P_1$=H and $R^P_2$=H;
Compound of Formula I: Z=—OCH$_2$CH=CH-phenyl, R1 and R2 taken together=O, R3=—CH$_3$, R4=—CH$_2$CH=CH$_2$, $R^P_1$=H and $R^P_2$=H;
Compound of Formula I: Z=—OCH$_2$CH=CH-phenyl, R1 and R2 taken together=O, R3=—CH$_3$, R4=—CH$_2$CH=CH-(3-pyridyl), $R^P_1$=H and $R^P_2$=H;

Compound of Formula I: Z=—OC(O)CH$_2$-(4-chlorophenyl), R1 and R2 taken together=O, R3=H, R4=—CH$_2$CH=CH$_2$, R$^P_1$=H and R$^P_2$=H; and Compound of Formula I: Z=—OC(O)CH$_2$-(4-chlorophenyl), R1 and R2 taken together=O, R3=H, R$_4$=—CH$_2$CH=CH-(3-pyridyl), R$^P_1$=H and R$^P_2$=H.

4. A pharmaceutical composition for treating bacterial infections comprising a therapeutically effective amount of a compound of claim 1 or a pharmaceutically acceptable salt, ester or prodrug thereof in combination with a pharmaceutically acceptable carrier.

5. A method for treating bacterial infections comprising administering to a mammal in need of such treatment a pharmaceutical composition containing a therapeutically-effective amount of a compound of claim 1 or a pharmaceutically acceptable salt, ester or prodrug thereof.

6. A process for the preparation of a compound represented by Formula I, as in claim 1 comprising:

(a) reacting a compound represented by the formula:

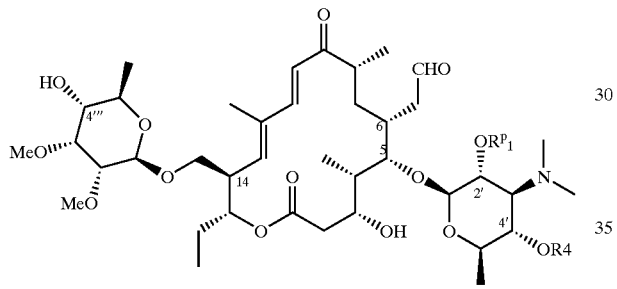

where R$^P_1$ is an ester or silyl ether and R4 is as defined in claim 1, with a silylating agent, optionally with the addition of 4-N,N-dimethylaminopyridine or imidazole, in an aprotic solvent between 0° C. to 100° C. to provide a compound represented by the formula:

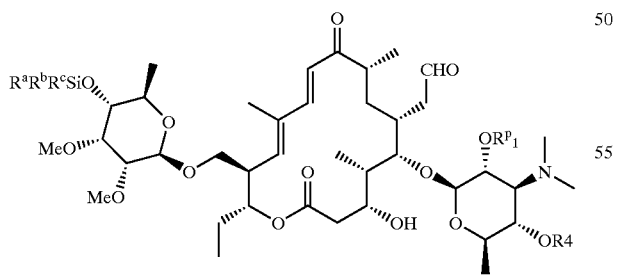

where R$^a$, R$^b$ and R$^c$ are each independently alkyl or aryl, R$^P_1$ and R4 are as defined previously;

(b) reacting the compound from step (a) with a hydride reducing agent in an organic solvent to provide a compound represented by the formula:

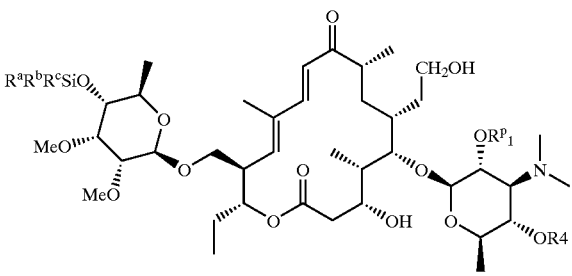

where R$^a$, R$^b$, R$^c$, R$^P_1$ and R4 are as previously defined;

(c) reacting the compound from step (b) with a halide compound of the formula Y-M-halide, where M and Y are as defined in claim 1, in the presence of a base in an aprotic organic solvent at a temperature between −20° C. to 60° C. to provide a compound represented by the formula:

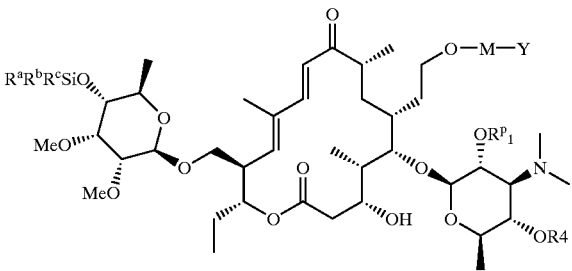

where R$^a$, R$^b$, R$^c$, R$^P_1$ and R4 are as previously defined;

(d) reacting the compound from step (c) with tetrabutylammonium fluoride or hydrofluoric acid to provide a compound represented by Formula I of claim 1, where Z=—O—M—Y, R1 and R2 taken together=O, R3=H, R$^P_2$=H, R$^P_1$ and R4 are as defined previously; and (e) reacting the compound from step (d) with methanol at a temperature between room temperature to reflux to provide a compound represented by Formula I of claim 1 where Z=—O—M—Y, R1 and R2 taken together=O, R3=H, R$^P_2$=H, R$^P_1$=H, R4, M and Y are as previously defined.

7. A process for the preparation of a compound represented by Formula I as defined in claim 1 comprising reacting a compound represented by the formula:

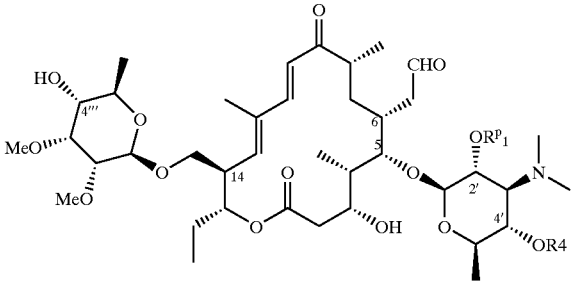

where $R^P_1$ and R4 are as defined in claim 1, with an amine in the presence of a borohydride reagent in an alcoholic solvent at a pH between 2 to 6, and optionally further reacting the resulting compound with methanol, to provide a compound represented by Formula I of claim 1, where Z=—NR7R8, R1 and R2 taken together=O, R3=H, $R^P_2$=H, $R^P_1$=H, R4 is as previously defined, and R7 and R8 are as defined in claim 1.

8. A process for the preparation of a compound represented by Formula I as defined in claim 1 comprising:

(a) reacting a compound represented by the formula:

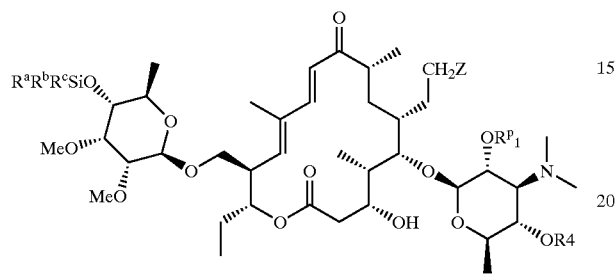

where Z and R4 are as defined in claim 1, $R^a$, $R^b$ and $R^c$ are each independently alkyl or aryl and $R^P_1$ is an ester or a silyl ether, with allyl bromide or propargyl bromide in the presence of a base in an aprotic solvent at a temperature between −20° C. to 60° C. to provide a compound represented by the formula:

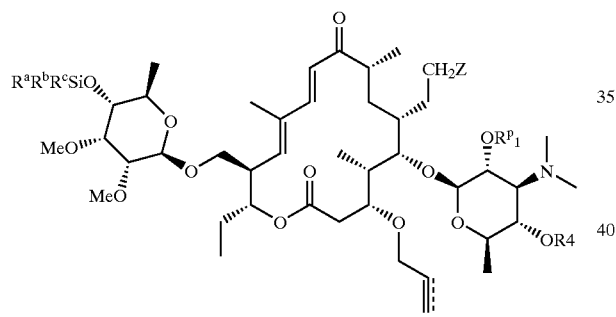

where Z, $R^a$, $R^b$, $R^c$, $R^P_1$ and R4 are as previously defined;

(b) reacting the compound from step (a) with an aryl halide or an aryl triflate, where the said aryl group is selected from an aryl, heteroaryl, substituted aryl, or substituted heteroaryl group in the presence of a palladium catalyst to provide a compound represented by the formula:

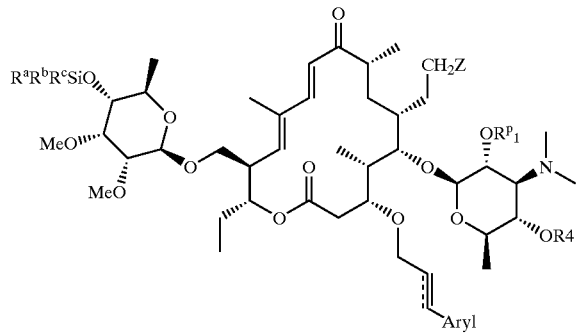

where Z, $R^a$, $R^b$, $R^c$, $R^P_1$ and R4 are as previously defined;

(c) reacting the compound from step (b) with tetrabutylammonium fluoride or hydrofluoric acid to provide a compound represented by the formula:

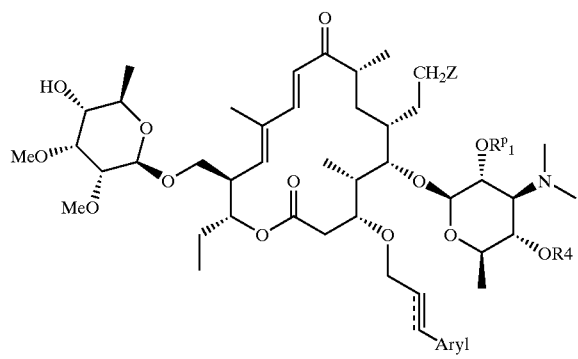

where $R^P_1$ is a hydroxy protecting group as previously defined, Z and R4 are as previously defined; and (d) reacting the compound from step (c) with methanol between room temperature to reflux to provide a compound represented by Formula I in claim 1, where Z and R4 are as defined in claim 1, R1 and R2 taken together=O, R3=—CH$_2$CC-Aryl or —CH$_2$CHCH-Aryl, and $R^P_1$ is H.

* * * * *